United States Patent [19]

Good et al.

[11] Patent Number: 4,689,297

[45] Date of Patent: Aug. 25, 1987

[54] DUST FREE PARTICULATE ENZYME FORMULATION

[75] Inventors: Ivan C. Good, Goshen; Yun C. Jao, Elkhart, both of Ind.

[73] Assignee: Miles Laboratories, Inc., Elkhart, Ind.

[21] Appl. No.: 708,584

[22] Filed: Mar. 5, 1985

[51] Int. Cl.$^4$ .................... C12N 11/00; C12N 11/14; C12N 11/02; C12N 9/98
[52] U.S. Cl. ........................ 435/174; 252/DIG. 12; 435/176; 435/177; 435/180; 435/187
[58] Field of Search .............. 435/187, 174, 176, 177, 435/180; 252/DIG. 12

[56] References Cited

U.S. PATENT DOCUMENTS

| | | | |
|---|---|---|---|
| 3,451,935 | 6/1969 | Roald et al. | 435/187 X |
| 3,519,570 | 7/1970 | McCarty | 252/135 |
| 3,650,961 | 3/1972 | Hudson | 252/DIG. 12 |
| 4,009,076 | 2/1977 | Green et al. | 195/63 |
| 4,016,040 | 4/1977 | Win et al. | 195/68 |
| 4,087,368 | 2/1978 | Borrello | 252/89 |
| 4,242,219 | 12/1980 | Bogerman et al. | 252/174 |
| 4,617,272 | 10/1986 | Kirkwood et al. | 435/183 |

FOREIGN PATENT DOCUMENTS

| | | |
|---|---|---|
| 2137042 | 7/1971 | Fed. Rep. of Germany . |
| 0151598 | 6/1980 | German Democratic Rep. . |
| 37983 | 2/1985 | Japan .................................. 435/187 |
| 1483591 | 7/1973 | United Kingdom . |

OTHER PUBLICATIONS

Preliminary Product Information—Novozyme ™ 243, Novo Industries, Denmark, 1983.
Final Product Information—Novozym ™ 243, Novo Industries, Denmark, 1984.

*Primary Examiner*—David M. Naff
*Attorney, Agent, or Firm*—Jerome L. Jeffers

[57] ABSTRACT

Dust free enzyme containing particles are produced by coating hydratable core particles with an enzyme and then with a film-forming macro-molecular material. Coating is carried out by suspending the core particles in a fluidized bed dryer, spraying an aqueous slurry of enzyme onto the core particles while suspended, and evaporating water to leave a dried enzyme coat on the particles. The resultant enzyme-coated particles, while still suspended in the fluidized bed, are sprayed with a solution or dispersion of the macro-molecular material, and dried to remove solvent to leave a coating of the macro-molecular material.

6 Claims, No Drawings

DUST FREE PARTICULATE ENZYME FORMULATION

BACKGROUND OF THE INVENTION

This invention relates to a procedure for making dry and dust free enzyme granules particularly useful for use with laundry detergents. The manufacture of enzymatic washing and cleaning agents by incorporating powdered, highly active enzyme concentrates by mixing them with common cleaning agents is well known. The washing agents manufactured in this manner tend to form enzyme dusts which can cause dermatologic damage both to the manufacturer and the consumer of the enzyme powder containing washing composition.

Various enzyme formulations and processes for these preparations have been developed in an effort to alleviate the dusting problem. For example, German AS No. 21 37 042 discloses a process in which an extrudable enzyme containing formulation is extruded through a die onto the revolving plate of a spheronizing device to form spherical particles of the enzyme containing formulations which are optionally coated with a material designed to prevent dusting.

In U.S. Pat. No. 4,087,368, there is disclosed an enzyme granule formulation in which rods or spheres of an enzyme in admixture with magnesium alkyl sulfate and ethylene oxide are provided.

U.S. Pat. No. 4,016,040 discloses a method for the preparation of free-flowing substantially dust free, spherical enzyme containing beads prepared by blending a powdered concentrate of the enzyme with a binder in molten form and spraying droplets of the blend through a spray nozzle into cool air to solidify the droplets and form the beads.

In U.S. Pat. No. 4,242,219, there is claimed a process for the preparation of enzyme containing particles prepared by mixing the dry enzyme with a hydrophilic organic cohesive material, a building agent and a moisture regulating agent and mechanically dividing it into particles of the desired size and shape which are then coated with a water repellent material.

Another type of granular enzyme formulation is described in U.S. Pat. No. 4,009,076. This formulation is prepared by mixing the dry enzyme with a solid non-viable substance and optionally a cohesive organic material as binder to form an enzymatically active core. An enzyme slurry containing the cohesive organic material can be sprayed onto, for example, sodium tripolyphosphate in a mixer or an enzyme powder can be mixed with the sodium tripolyphosphate and the cohesive organic material sprayed onto it with subsequent extrusion through a die. The enzyme containing granule is sprayed with an aqueous solution containing a plasticized organic resin and then dried.

A process is described in DDR Pat. No. 0 151 598 in which sodium tripolyphosphate is sprayed with an aqueous enzyme solution and agglomerated in a cyclone apparatus. The agglomerates are removed from the cyclone apparatus while still wet and placed in a mechanical blender with a drying detergent formulation and intensively mixed.

In British Pat. No. 1,483,591, there is described a process for coating water soluble or water dispersible particles, including enzyme particles, using a fluid bed reactor. This reference involves a dust free coating technique for enzyme particles which have been granulated by other processes such as prilling or spheronizing whereas the process of this disclosure applies an active layer of enzyme onto an inert core.

SUMMARY OF THE INVENTION

The present invention is a method for the production of dust free enzyme containing particles. The method comprises the steps of:

(a) introducing a particulate, hydratable core material into a fluid bed dryer and maintaining the core particles suspended in the dryer's reaction chamber;

(b) providing an aqueous slurry of a water soluble or dispersible enzyme and applying the enzyme to the surface of the core particles by spraying the slurry onto them while they are suspended in the reaction chamber to leave residual, dried enzyme coated on the core particles in an amount sufficient to provide the desired enzyme activity;

(c) spraying a solution or dispersion of a macromolecular, film-forming, water soluble or water dispersible coating agent onto the enzyme coated core material while it is still suspended in the reaction chamber and drying the solvent to leave a continuous layer of the film-forming material on the enzyme coated core particle to provide the desired dust free enzyme containing particle.

Also included within the scope of this invention are the enzyme containing particles prepared by this process.

DESCRIPTION OF THE INVENTION

The method of the present invention is carried out in a fluid bed dryer. Typically, such devices comprise a dryer consisting of a circular product chamber that has a porous grid on the bottom and is open on the top to be put up against a conical shaped expansion chamber of a larger diameter than the circular product chamber. In operation, as the velocity of air passing up through the chamber is increased, a point is reached where particles resting on the porous grid are suspended in the air flow as a fluid, hence the terms "fluidization" and "fluid bed dryer". The particles are lifted by the upward force of the air out of the product chamber into the expansion chamber where the air expands and the upward force per unit of area is reduced. This allows the particles to fall back into the product chamber and start the cycle over.

The initial step in the method involves introducing a particulate, hydratable core material into the reaction chamber of the fluidized bed reactor and suspending the particles therein on a stream of air. The core particles are preferably of a highly hydratable material, i.e. a material which is readily dispersible or soluble in water. The core material should either disperse (fall apart by failure to maintain its integrity) or solubilize by going into a true solution. Clays (bentonite, kaolin), non-pareils and agglomerated potato starch are considered dispersible. Non-pareils are spherical particles consisting of a solid core that has been rounded into a spherical shape by binding layers of powder to the core in a rotating spherical container. The non-pareils used in the examples which follow have a sugar (typically sucrose) crystal core (−50 mesh on the U.S. Standard Sieve Series) that was rounded by binding layers of corn starch onto the core using sugar as a binder. The sugar used for binding was dissolved in water (50% w/w) and sprayed onto a mixture of sugar and corn starch while they were being rotated in a 66 inch Groen Stainless Steel Rotating Pan which were then heated to drive off the water. When the crystals had been rounded into approximately 20 mesh to 60 mesh spheres, they were dried and sieved whereupon the −20 mesh +60 mesh fractions were put back into the rotating pan and heated. They were then coated with a layer (approximately 10% w/w) of dextrin from an aqueous solution (50% w/w) that was sprayed onto the spheres while heating to drive off the water. The finished product was again sieved to −20 mesh +60 mesh. Salt particles (NaCl crystals, NaCl rock salt, NaHCO$_3$) are considered soluble. More particularly, core particles can be non-pareils of a salt crystal, starch and a sugar solution or a sugar crystal, starch and a sugar solution with or without a final coat of dextrin or a confectionary glaze. Also suitable are agglomerated trisodium citrate, pan crystallized NaCl flakes, bentonite granules and prills, bentonite/kaolin/diatomaceous earth disk pelletized granules and sodium citrate crystals. The core particle is of a material which is not dissolved during the subsequent spraying process and is of a particle size of from 150 to 2,000 microns (100 mesh to 10 mesh on the U.S. Standard Sieve Series) in its longest dimension.

Enzymes suitable for use in this method are those which are soluble or dispersible in an aqueous media and from which the water can be removed to leave a residual layer of enzyme on the surface of the core material. Suitable enzymes include, for example, proteases (bacterial, fungal, acid, neutral or alkaline), amylases (alpha and beta) and lipases whose water solutions or dispersions are prepared by dispersing or dissolving a precipitated enzyme cake in water using vigorous agitation. Typically, the enzyme precipitate is dissolved or dispersed at a level of 15% to 30% solids (w/w) of which 100% down to about 30% is enzyme with the remaining solids comprising metallic salts, binders, plasticizers and fragrances. The dispersion, including any optional binders, metallic salts, stabilizers or fragrances must have a viscosity low enough (typically 10 to 5,000 cps at room temperature) to be pumped and atomized for effective spray coating. The enzyme is applied to the surface of the core material by fluidizing the core particles in a flow of air whereupon a solution containing the enzyme and optionally other solids is then atomized and sprayed into the fluidized bed. The atomized droplets contact the surface of the core particles leaving a film of the solids adhering to the surface of the particles when the water is evaporated.

When sufficient enzyme is applied to the core particles to provide the desired enzyme activity, the enzyme coated particles, while still suspended in the reaction chamber of the fluidized bed reactor, are coated with a uniform layer of a water soluble or water dispersible, macro-molecular, film-forming coating agent. This is accomplished in a manner similar to that used for application of the enzyme coating. Suitable film-forming agents include, for example, fatty acid esters, alkoxylated alcohols, polyvinyl alcohols, ethoxylated alkylphenols and more specifically, polyethylene glycols (MW 1,000 to 8,000), linear alcohol alkoxylates (MW 1,450 to 2,670), polyvinyl pyrrolidone (MW 26,000 to 33,000), polymeric nonylphenyl ethoxylates (MW 1,975 to 4,315) and dinonylphenyl ethoxylate (average MW 6,900). The net result of the process is to provide an enzyme coated core particle having a continuous layer of the film-forming material on its surface to provide the desired dust free enzyme containing particle.

The dust free enzyme particles of the present invention can be used wherever enzymes are needed in an aqueous system. Thus, they can be used as additives to detergent formulations, for removing gelatin coatings on photographic films to aid in silver recovery, in the digestion of wastes from food processing plants for nitrogen recovery, in denture cleansers for removing protein bound stains and as a processing aid in waste water treatment.

The method of practicing the invention is further illustrated by the following examples where all mesh sizes are on the U.S. Standard Sieve Series, and the dryer is a Uni-Glatt laboratory model fluid bed dryer with variable air temperature and flow through the bed. The device has a 6 inch Wurster insert which consists of a container (5½" diameter by 6½" height) for the core material that fits against the bottom of the device's expansion chamber. The plate on the bottom of the Wurster has holes in it to distribute the air through the bed with the holes in the center being of a larger diameter than the rest of the holes in the plate. A cylindrical hollow tube (2¾ inches diameter by 6 inches length) called a partition is suspended above these larger diameter holes creating a higher air flow up through the partition than up around the outside of the partition. The air flow is adjusted based on the quantity and density of the core particles so that the particles flow up inside the partition into the expansion chamber then fall back down outside the partition into the area with less air flow while the bed is kept fluidizing and drying. This difference in air flow creates a circular upward and downward movement of the particles. The spray nozzle is installed at the bottom of the partition pointed upwards. This arrangement keeps the atomized liquid co-current with the motion of the cores being coated and results in a smooth coating. The speed of the circular flowing motion of the cores is adjustable by regulating the amount of air going through the partition and the amount of air going around the outside of the partition. The droplet size of the atomized enzyme solution spray is adjusted by adjusting the liquid pumping rate and the air pressure for atomization. The process can be accelerated by using counter current downward spray without using the Wurster column.

The height of the Wurster insert partition is adjustable vertically and was adjusted from ¼ inch to ¾ inch up from the bottom plate. When denser core materials are used, up to ¾ of the holes outside the partition were blocked off to provide a higher linear velocity for the air to lift the particles up through the inside of the partition and maintain a smooth circulation of material through the spraying area. The total air flow was adjusted to get a good flow of cores through the partition and keep the bed outside the partition fluidized. Inlet air temperature was adjusted up to a maximum of 75° C. so that the outlet as well as particle temperatures were below 50° C. Typical outlet temperatures during the coating process were 25° C. to 40° C. The solids level of enzyme slurry sprayed in was 15% to 30% of the solution (w/w). Feed rate varied from 5 ml/min. to 20 ml/min. When a more soluble core material was used, a lower initial feed rate was essential to coat a layer of enzymes on the core before the feed rate was increased. Atomization air pressure ranged from 1.0 to 1.5 bar. A typical dry weight gain of the core material after enzyme coating is 10% to 35% depending on the final activity desired. The enzyme coated core was further coated with a macro-molecular, film-forming, water soluble or water dispersible coating agent to seal the enzyme from contact with the atmosphere or persons handling the particle. After application of the enzyme and protective coating, the typical total dry weight gain based on the weight of the core material after the dust free coating is 25% to 55%.

In the following examples, the core materials are either salt or non-pareils. Salt is totally soluble and water clear when dissolved and is inexpensive as a core material. Being a solid crystal and not a multicompound structure, it is less subject to breaking up during the coating process and the enzyme slurry can be sprayed at a faster rate. However, the salt particles being cubes make them more difficult to coat because there is a greater tendency for poor binding between the film and the core. Furthermore, enzyme coated salt crystals are more subject to film loss due to attrition from the corners of cubes striking the flat surfaces of others. This problem can be partially alleviated by adding binders or plasticizers to the enzyme slurry. Suitable materials include carboxymethyl cellulose, sodium alginate, collagen, polyethylene glycol and ethoxylated alkylphenols in an amount of from 1 to 10% (w/w) of the total solids in the slurry. In addition, the flat surfaces provide larger areas of contact between particles which can cause agglomeration thereby inhibiting the flow characteristics of the coated salt particles. The non-pareils are spherical, can readily be coated with a continuous film and have less area of contact among particles thereby limiting agglomeration. The final spherical product has better flow characteristics than the cubic salt based enzyme product.

EXAMPLE 1

Laboratory Fluid Bed Spray Coating of Alkaline Protease

Eight hundred and eighty-five grams of non-pareil particles (prepared by spraying a sugar solution onto sugar crystals which were coated with starch followed by a final coat of dextrin, −30 +60 mesh) were charged to the Uni-Glatt device previously described and fluidized. An aqueous enzyme slurry with 16% dry solid at the detergent alkaline protease level of 650 DAPU/gm (DAPU=Detergent Alkaline Protease Unit) was fed into the dryer for coating at the rate of 8 ml/minute. A total of 716 g of enzyme slurry containing 115 g of enzyme solid was sprayed onto the particles.

The enzyme coated particles were further coated with a nonylphenol ethoxylate having an average molecular weight of 4315 marketed under the trademark Inconol NP-100 (BASF-Wyandott Corp.) by spraying 120 g of its aqueous solution onto the particles in the Uni-Glatt device. The solution, which was 50% w/w, contained 60 g of the Iconol NP-100 and was sprayed at a rate of 8 ml/minute. Iconol NP is a nonionic chemical compound composed of a nonylphenol hydro-phobe and a polyoxyethylene group hydrophile all in one molecule. The material is represented by the structural formula:

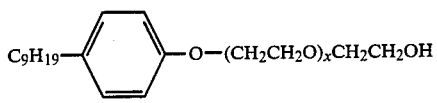

with X being approximately 100 in the NP-100 material.

The coated particles were further cosmetically coated with 260 g of an aqueous solution containing 82 g (31.5% w/w) tantanium dioxide and 27 g (10.4% w/w) Iconol NP-100 at the feed rate of 8 ml/minute.

A final total of 1116 g dust free particles was harvested with a final activity of 390 DAPU/g as determined by Detergent Alkaline Protease Units Procedure, Miles Laboratories, Inc. QA Procedure #ME400.23 available from Miles Laboratories, Inc., Enzyme Technical Service Department, P.O. Box 932, Elkhart, IN 46515. This test resulted in 100% mass balance yield and 96% of enzyme yield.

The Uni-Glatt operation conditions were as follows:

| | |
|---|---|
| Air Regulation Flap Level: | Fully Open |
| Product Pressure Differential: | 0.5 Kilo-pascals |
| Outlet Air Pressure Differential: | 200-250 mm Water |
| Atomization Air Pressure: | 1.5 Bar |
| Inlet Air Temperature Setting: | 60/64° C. and 50–54° C. |
| Outlet Air Temperature Range: | 30–40° C. |
| 6 inch Wurster Insert | |
| Clearance from Bottom Plate: | ¼ inch |
| Angle setting: | 3 mm |

EXAMPLE 2

Laboratory Fluid Bed Spray Coating of Both Alkaline Protease and Alpha-Amylase

In this run, the Uni-Glatt operating conditions were the same as in Example 1 except that the Wurster insert was ¾ inch from the bottom plate and the inlet temperature was in the 70°–74° C. range.

One thousand grams of −30 +60 mesh non-pareils (sugar crystals-sugar solution-starch-dextrin-glaze) was charged to the Uni-Glatt and fluidized. An aqueous enzyme slurry with 19% (w/w) dry solid having activity of 643.8 DAPU/g and 252,632 MWU/g (modified Wohlgemuth unit per gram) was fed into the dryer for coating at the rate of 12 ml/min. A total of 2000 g of enzyme slurry containing 380 g of enzyme solid was used.

The enzyme coated particles were further coated with 146 g of a 50% (w/w) solution containing 73 g of polyethylene glycol (MW 4000) in water at a feed rate of 12 ml/min. and an inlet air temperature of 50°–54° C.

A final total of 1453 g of dust free particles was harvested with a final activity of 846 DAPU/g and 339,045 MWU/g as determined by the Wohlgemuth Alpha-Amylase Procedure, Miles Laboratories, Inc. Enzyme Approved QA Procedure #ME400.03. This test resulted in a recovery of 100% of mass balance yield and a 97.5% recovery of enzyme activity.

EXAMPLE 3

Pilot Scale Fluid Bed Coating of Alkaline Protease

Fifty kilograms of −30 +60 mesh NaCl salt crystals were charged and fluidized in a Glatt fluid bed dryer model GPCG-60 with an 18" Wurster insert. Aqueous enzyme slurry at 813.5 DAPU/g with an 18% dry solid content was fed into the dryer for coating at the rate of 125 ml/min. for the first 10 minutes, 200 ml/min. for 110 minutes, 300 ml/min. for 40 minutes, and 450 ml/min. for 20 minutes for a total of 6.858 kg enzyme solid from 38.1 kg of slurry.

The enzyme coated salt crystals were further coated with 20.3 kg of a solution containing 6.1 kg (30% w/w) Iconol NP-100 in water at the feed rate of 125 ml/min.

for 80 minutes, 167 ml/min. for 30 minutes, and 227 ml/min. for 22 minutes.

A final total of 61.1 kg dust free particles were harvested with a final activity of 354 DAPU/g. This experiment resulted in a 99.5% mass balance yield and 72.2% enzyme activity yield.

The GPCG-60 fluidized bed dryer is a production model fluid bed spray coater very similar in design to the Uni-Glatt except that it has a proportionally taller expansion chamber. It was operated under the following conditions:

| Air Regulation Flap: | Varies |
| --- | --- |
| Partition Height: | 1 inch clearance from bottom plate |
| Nozzle Size: | 1.8 mm |
| Inlet Air Temperature: | 70–74° C. and 50–54° C. |
| Outlet Air Temperature: | 29–32° C. |
| Angle Setting: | 6 mm |
| Atomization Air Pressure: | 4 Bar |
| 18 inch Wurster Insert | |

EXAMPLE 4

Pilot Scale Fluid Bed Spray Coating of Alkaline Protease

Forty and seventeen one-hundredths kilogram of −30 +60 mesh non-pareil (sugar crystals-sugar solution-starch-dextrin) was charged and fluidized in a GPCG-60 with exactly the same setup and operating conditions as in Example 3. Enzyme slurry at 813.5 DAPU/g with 18% dry solid was fed into the dryer for coating at the rate of 75 ml/min. for the first 30 minutes, increased from 75 to 400 ml/min. steadily in the following 110 minutes and then maintained at that rate for the remainder of the run. A total of 45.2 kg of enzyme slurry was used to apply 8.136 kg of enzyme solid to the core particles.

The enzyme coated particles were further coated with 9.7 kg of a solution containing 2.91 kg (30% w/w) Iconol NP-100 in water at the flat feed rate of 36 ml/min. for 81 minutes.

The particles were further coated with 11.6 kg of an aqueous solution containing 3.48 kg $TiO_2$ (30% w/w) and 1.39 Iconol NP-100 (12% w/w) at the feed rate of 50 to 55 ml/min. for 214 minutes.

A final total of 55.2 kg was harvested with a final activity of 646 DAPU/g. This test resulted in 97.6% mass yield and 97% activity yield.

EXAMPLE 5

Pilot Scale Fluid Bed Downward Spray Coating of Alkaline Protease

In this experiment a GPCG-5 fluidized bed dryer manufactured by Glatt Air Techniques with a single air atomized Schlick nozzle, as was the case in the previous examples, located concentrically 14.5 inches high from the bottom of the product bowl was used. Core material particles were fluidized by the inlet air to a height of 6 to 12 inches above the nozzle which enabled the coated particles to become dry before falling back down onto the product bowl. This operation mode minimizes particle agglomerization.

Ten kilograms of salt crystals were charged to the product bowl of the fluidized bed reactor and fluidized with 70° C. inlet air to a product temperature of 45° C., as determined by a probe in the bed, whereupon enzyme slurry was sprayed into the area of fluidized core material. The slurry, which contained 16% dry solid with an enzyme activity of 434.7 DAPU/g, was fed at a steady rate of 190 g/min. The product temperature was consequently maintained at a steady range of 34°–38° under these inflow and outflow conditions.

The enzyme coated particles were further coated with 2.6 kg of an aqueous solution containing 50% (w/w) Iconol NP-100 and 50% water. The solution was atomized at a spray rate of 70 g/min. at 50° C. inlet temperature. Holding the inlet air at 50° C. resulted in a product temperature of 37° to 41° C.

A final weight of 12.7 kilograms of dust free particles was harvested with a final activity of 305.9 DAPU/g. This test resulted in a 99.7% mass balance yield without activity loss.

GPCG-5 Operating Conditions:

| Air Regulation Flaps: | Inlet 100% Outlet 38% |
| --- | --- |
| Atomization Air Pressure: | 4 Bar |
| Nozzle Size: | 1.2 mm |
| Angle Setting: | 4.0 mm |
| Inlet Air Temperature: | 70° C. and 50° C. |
| Product Temperature: | 34–41° C. |
| Air Inlet Filter Pressure: | 50 mm $H_2O$ |
| Product Bed Pressure: | 30 mm $H_2O$ |
| Exhaust Air Filter Pressure: | 150 mm $H_2O$ |

What is claimed is:

1. A method for the production of dust free enzyme containing particles which comprises the steps of:
   (a) introducing a particulate, core material which is readily dispersible or soluble in water and has a particle size of from 150 to 2,000 microns in its longest dimension into a fluidized bed dryer having a production chamber and maintaining the particulate material suspended in the dryer's product chamber;
   (b) providing an aqueous slurry of a water soluble or dispersible enzyme wherein the slurry contains 15% to 30% solids (w/w) of which 100% to 30% is enzyme and has a viscosity of 10 to 5,000 cps. at room temperature and applying the enzyme to the surface of the particulate core material by spraying the slurry onto the particulate core material while it is suspended in the product chamber and evaporating water to leave residual, dried enzyme coated on the particulate core material in an amount sufficient to provide a desired enzyme activity; and
   (c) spraying a solution or dispersion of a macromolecular, film-forming, water soluble or water dispersible coating agent onto the enzyme coated particulate core material while it is still suspended in the product chamber and drying to remove solvent to leave a continuous layer of the film-forming material on the enzyme coated particulate core material wherein there is applied sufficient enzyme and film-forming material to provide a total dry weight gain of 25% to 55% based on the weight of the particulate core material to thereby provide the desired dust free enzyme containing particles.

2. The method of claim 1 wherein the particulate core material is clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, Kaolin and diatomaceous earth or sodium citrate crystals.

3. The method of claim 1 wherein the enzyme is a protease, an amylase or a lipase.

4. The method of claim 1 wherein the film-forming material is a fatty acid ester, an alkoxylated alcohol, a polyvinyl alcohol, or an ethoxylated alkylphenol.

5. The method of claim 1 wherein the film-forming material is a polyethylene glycol having a molecular weight of from 1,000 to 8,000, a linear alcohol alkoxylate having a molecular weight of from 1,450 to 2,670, a polyvinyl pyrrolidone having a molecular weight of from 26,000 to 33,000, polymeric nonylphenyl ethoxylates having a molecular weight of from 1,975 to 4,315 or a polymeric dinonylphenyl ethoxylate having an average molecular weight of 6,900.

6. An enzyme containing particle prepared by the method of claim 1.

* * * * *